United States Patent [19]

Hohmann et al.

[11] Patent Number: 4,824,366

[45] Date of Patent: Apr. 25, 1989

[54] METHOD AND APPARATUS FOR REMOVAL OF OBJECTS GLUED ONTO DENTAL ENAMEL, IN PARTICULAR BRACKETS

[75] Inventors: Wolfgang Hohmann, Berlin; Peter-Michael Schopf, Bad Vilbel; Klaus Gerkhardt, Worms; Bogdan Kocjancic, Frankfurt, all of Fed. Rep. of Germany

[73] Assignee: Scheu-Dental Inhaber Rudolf Scheu, Iserlohn, Fed. Rep. of Germany

[21] Appl. No.: 55,712

[22] PCT Filed: Aug. 30, 1986

[86] PCT No.: PCT/DE86/00346

§ 371 Date: May 7, 1987

§ 102(e) Date: May 7, 1987

[87] PCT Pub. No.: WO87/01577

PCT Pub. Date: Mar. 26, 1987

[30] Foreign Application Priority Data

Sep. 13, 1985 [DE] Fed. Rep. of Germany ....... 3532656

[51] Int. Cl.⁴ .................................................. A61C 3/00
[52] U.S. Cl. ....................................... 433/32; 219/234
[58] Field of Search ................. 433/32, 3, 4; 219/227, 219/234, 230

[56] References Cited

U.S. PATENT DOCUMENTS

| | | | |
|---|---|---|---|
| 3,924,332 | 12/1975 | Rauch et al. | 219/234 X |
| 4,034,762 | 7/1977 | Cosens et al. | 219/234 X |
| 4,375,961 | 3/1983 | Brooks | 433/4 |
| 4,441,013 | 4/1984 | Masreliez | 219/234 X |
| 4,455,138 | 6/1984 | Sheridan | 433/3 |
| 4,553,021 | 11/1985 | Conti | 219/234 |

FOREIGN PATENT DOCUMENTS 2177047 11/1973 France.
719821 3/1980 U.S.S.R. ................ 219/234

Primary Examiner—Samuel Scott
Assistant Examiner—Noah Kamen
Attorney, Agent, or Firm—Toren, McGeady & Associates

[57] ABSTRACT

A control of the adhesive layer is to be achieved with a process and a device for removal of brackets or other metallic dental objects serving for orthodontic treatment which have been glued onto dental enamel wherein the layer of glue between the bracket or the object and the dental enamel is to be reduced in its adhesiveness by heating, wherein the tooth of the patient is effectively protected in such a way that a heating of the tooth itself cannot even occur. This is achieved in that the heating is performed by direct electrical resistance heating.

5 Claims, 1 Drawing Sheet

METHOD AND APPARATUS FOR REMOVAL OF OBJECTS GLUED ONTO DENTAL ENAMEL, IN PARTICULAR BRACKETS

FIELD OF THE INVENTION

The invention is directed to a method and apparatus for removal of brackets or other metallic dental objects serving for orthodontic treatment which have been glued onto dental enamel, wherein the adhesiveness of the adhesive layer between the bracket or the object and the dental enamel is reduced by application of heat.

DESCRIPTION OF RELATED ART

It is known to glue brackets onto the outer surface of teeth in the course of regulating measures of dental treatment, which are subjected to a permanent load in a predetermined position by means of appropriate tightening wires, in order to make the tooth in this manner assume, little by little, the desired position. Since a comparatively high load acts on the brackets, the connection with the surface of the tooth must be as solid as possible. A possibility consists in that the brackets are fastened mechanically to the tooth by means of metal slings. Another possibility consists in gluing the brackets to the teeth, and only this method will be discussed in the present invention.

In order to increase the adhesion of the glue to the tooth, the surface of the tooth is etched, in order to achieve a sponge-like increase of this surface.

If a durable connection of the brackets with the teeth to be treated in the course of orthodontic treatment is particularly desirable, then a problem arises involving the removal of the brackets after the treatment is finished. Hitherto it has been usual to mechanically remove the brackets wherein damage to the tooth has to be accepted. In this type of removal, the bracket is gripped, for instance, with a forceps and is forcefully sheared off the tooth by a twist, twisted or levered off, in the course of which the adhesive layer is to be torn apart. Herein, there arises the danger that the tooth enamel is also torn off.

An instrument is known from the US-PS No. 4 455 138 which can be engaged with a heatable blade into a recess in the brackets. The user holds herein the instrument for as long at the bracket until the hot blade has heated said bracket to such an extent that the heat has reduced the adhesiveness of the glue. The bracket can then be sheared off with the blade-shaped instrument.

A particular disadvantage of this known instrument consists in that the hot instrument can touch the patient in the course of unexpected movements of the head of the patient or during other interference, so that this can then cause local burns. Also an overheating of the tooth itself can occur entailing disadvantages which will be described later.

DISCLOSURE OF THE INVENTION

Compared to this, it is the task of the invention to achieve such a control of the adhesive layer that the tooth of the patient is protected in a lasting manner, in such a way that heating of the tooth itself cannot occur.

In a method of the previously described type, this task is solved in the invention by performing the heating by means of a direct electrical resistance heating. By heating the bracket through electrical resistances, it is achieved that, to begin with, the tool remains completely cold; in the course of handling errors, no burning of the patient can thus occur. Also resistance heating of metallic objects is particularly suitable, because the treatment can occupy a very short time period, since the metallic objects are heated very rapidly by means of a resistance heater and therefore a rapid detachment of the adhesive coating can occur.

The invention makes use of the composition of the glues which are utilized which, as a rule, represent plastic bound composites, the adhesiveness of which can be largely controlled by heat application. By heating this in practice very thin adhesive layer the adhesiveness is greatly reduced and the glued-on bracket can be easily lifted off. This can occur so that the individual bracket remains undamaged which was not assured in the previous tearing off or shearing off, so that the bracket nowadays can be reused.

In a refinement, the invention provides that the heating is performed as a short duration heating, as this has already been described above. The application of the required energy can be performed in many different ways. Thus the invention provides in one embodiment, that the frequency resistance heating is performed by a succession of high-frequency alternating current pulses, whereby the invention can equally provide that the resistance heating is performed by a DC current source.

The method is designed appropriately in such a way that the resistance heating is applied by a forceps- or tweezer-like gripping instrument. If, namely, the dental objects which have to be glued to the teeth are overheated, then we are dealing with temperatures of up to 200° C. in the case of adhesives which are to be used, and the metallic object is heated up to that temperature in a very short time. Therefore it is sensible to grip this object directly, so that it indeed detaches itself in the heated state from the tooth, subsequently, however, it does not fall into the mouth cavity and cause burns there. In refinement, the invention provides that the gripping instrument is connectible to a DC current source, wherein the DC current source supplies a high current strength at low voltage for a comparatively short time period, wherein it is especially provided that DC or also AC voltages of 2 volts and a current pulse of up to 1 kilo ampere is used during a time interval of several milliseconds.

Voltage, type of current, and current strength can naturally deviate from the ranges indicated here. These ranges lie particularly to suit the type of metals of the dental objects or the like which are being utilized.

An essential factor in the detachment of brackets by heat application is to be seen in that a tooth cannot be heated to a higher temperature than 56° C. on its inside, in order to avoid biological damage, meaning in order to eliminate the danger that the body protein begins to coagulate. In order to eliminate this danger with certainty, a maximum inside temperature of the tooth of 45° C. should not be exceeded. The attainment of this temperature depends naturally on the temperature of heating the brackets and its duration, meaning how long this heat is allowed to act upon the tooth. In the case of an indirect heating with for instance a heated instrument, temperatures of 150° C. should not be exceeded and the duration should not exceed approximately 8 seconds.

In the case of direct heating these sets of circumstances can slightly vary. Here the brackets can attain a peak temperature of 200C, since this is only the case for fractions of seconds; thus one does not run the risk of heating the tooth above the desired inside temperature of 45 C.

For the solution of the task defined above, the invention provides also a somewhat different sort of controlling the adhesive glue coating. This application of energy to the adhesive layer consists in a modified process of the invention in that the adhesiveness is reduced by ultrasonics.

It is basically known to utilize ultrasonic technology for instance during removal of tooth tartar.

The task defined above is solved in a device particularly for performing the process described above with a temperature influence according to the invention in that the device consists of two forceps-like gripping legs electrically insulated form each other, which are connectible with a source supplying DC or AC current.

This tweezer or forceps-like instrument has the advantage that on the one hand it can hold a bracket and on the other hand the required energy can be supplied directly through this instrument in order to heat the adhesive layer.

In a particularly appropriate embodiment, the invention also provides that the device comprise a protective circuit in such a way that the higher current pulse can be triggered only when the electric contact between the object to be detached and the gripping legs of the gripping tool has been established.

This type of design has the special advantage that no faulty actuation can occur, for instance that by touching the tweezer arms these can already be heated to such an extent prior to gripping the bracket, that this can possibly result in injuring the patient.

The invention also provides that it is equipped with a condenser battery for producing the high current pulse, whose pulse is released by a current circuit element.

Other appropriate embodiments consist in equipping the tweezer legs with at least partially replaceable gripping ends adapted to the respective objects, and the invention provides additionally that the device is equipped with an optical and/or acoustic contact indication, i.e., a light or sound indicator that proper electrical contact between the gripping tool and the object has been established.

The device can also be connected with a time relay if the layout may render this necessary.

This timing relay has the special task of preventing a multiple consecutive energy application to the brackets at too short intervals. If namely the device according to the invention is used at too short intervals in order to be applied to the brackets, there exists the danger that these are heated to such an extent that the tooth can be damaged by this, it can easily result in the brackets becoming red hot. The timing relay prevents this through a blockage, which prevents the apparatus from operating until a cooling of the brackets has occurred with certainty.

BRIEF DESCRIPTION OF THE DRAWING

In the following, the invention is described with particularity with the help of a drawing by way of an example in which.

DESCRIPTION OF THE PREFERRED EMBODIMENT

Figure 1:
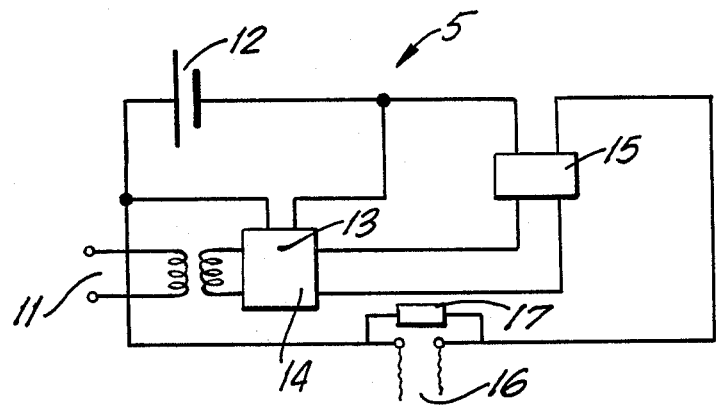
FIG. 1 shows the design of the DC current source in simplified presentation.
Figure 2:
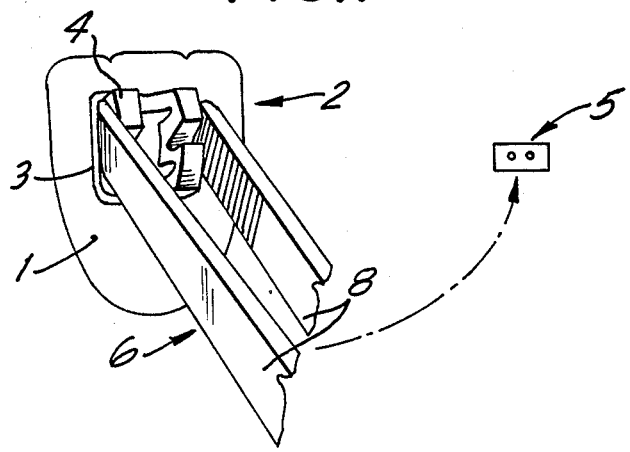
FIG. 2 shows a bracket glued to a tooth.
Figure 3:
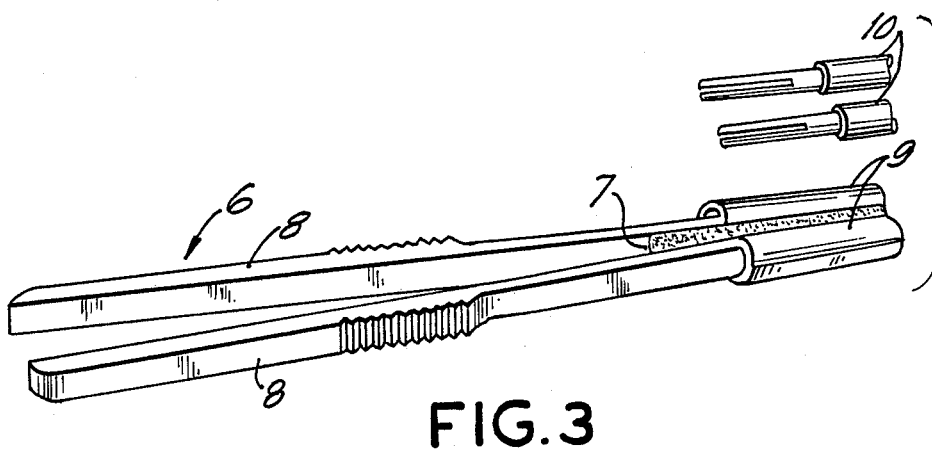
FIG. 3 shows a three-dimensional illustration of this example of a gripping instrument.

The device according to the invention for detaching of the bracket 4 glued, by means of an adhesive layer 3, to the surface 1 of a tooth 2, consists essentially of a DC current source generally designated with 5 and a gripping instrument generally designated with 6.

The gripping instrument 6 exhibits two gripping legs 8 connected with each other through an insulation 7. The gripping legs 8 are equipped with plug-in sockets 9, into which plugs 10 of a connecting cable are insertable by means of which the gripping instrument 6 can be connected with the DC current source 5.

The DC current source 5, depicted in FIG. 1, is designed essentially similar to a battery charger and is, for this purpose, equipped with a detachable power supply connection 11 for, for instance, 220 volts at 50 Hz. The battery to be charged is designated with 12. The output of the battery charger is designated with 13. A timing relay 14 is provided in the battery charger, wherein the apparatus overall is actuatable by means of a circuit breaker 15. The cable ends connected with the power plugs 10 are designated with 16 in FIG. 1

The essential functions of the circuit illustrated in a simplified manner in the FIG. 1 consists in supplying the instrument 6 during short time intervals with a comparatively low voltage of approximately 2 volts with a comparatively high current strength of 100 amperes or more, and indeed within a very short time period of several milliseconds.

For instance, the operator switches on the DC current source 5 through the circuit breaker 15, for instance, by actuating a food pedal (not shown) with simultaneous application of the legs 8 to the bracket 4. The DC current source 5 then supplies a voltage of 2 volts for several milliseconds with a current intensity of 100 amperes or higher between the ends of the two gripping legs 8, which use the bracket 4 as a resistance clamped between them. The bracket 4 is heated by the direct current flow and yields its heat then also to the adhesive layer 3. By heating of the adhesive layer its adhesiveness is greatly reduced so that the bracket 4 can be easily lifted off with the gripping instrument 6 without the surface 1 of the tooth 2 being damaged.

The timing delay 14 assures that between two switching processes a certain time interval must elapse, which is adjusted in such a way that an indeed heated bracket 4, however a bracket not yet removed, had sufficient time to adequately cool prior to renewed gripping and heating by the tweezers 6. A suitable indicator 17, such as a light or sounding device, can be connected to the output 16 to indicate when the proper contact has been established between the instrument legs 8 and the bracket 4.

Naturally, the described embodiment of the invention can be changed in many respects without abandoning the basic thought. Thus the invention is not limited to the special type of the forceps leg design, also not to the indicated current-and voltage values and also not to the time intervals indicated. Depending on the type of alloy in the bracket 4, other current values, voltages and time intervals can be provided. Thus the direct current source itself can be equipped with an appropriate control which is to be adjusted by the operator which however has not been depicted in detail.

We claim:

1. Device for safe removal of brackets or like metallic dental objects glued to dental enamel and serving for orthodontic treatment by heating the glued objects by direct electric resistance heating, said device comprising:
   - a forceps- or tweezer-like gripping instrument with two forceps-like gripping legs electrically insulated from each other and whose ends are configured to directly grip the glued object to establish a low resistance series circuit of the gripping legs and object and capable when the glue weakens to remove the bracket,
   - a source of low voltage, high current pulses having a short time interval,
   - and means for connecting the pulse source to the gripping legs, the current pulses having characteristics such that application of such a pulse to the gripped object will by direct electric resistance heating of the object sufficiently raise the temperature of the glue so that the glue becomes weakened and thus allows the instrument to readily remove the gripped object without over-heating the dental enamel.

2. Device as claimed in claim 1, wherein the pulse source includes a protective circuit for applying the pulse to the instrument only after the low resistance series circuit between the gripping legs and the object has been established.

3. Device as claimed in claim 1 or 2, wherein the pulse source comprises a battery in a charging circuit for producing the high current pulse.

4. Device as claimed in claim 1, wherein the gripping leg ends have at least partially replaceable gripping ends configured for gripping the object.

5. Device as claimed in claim 1 or 2, wherein the pulse source comprises means for indicating when the low resistance series circuit has been established.

* * * * *